(12) United States Patent
Brotz (10) Patent No.: US 6,443,616 B1
(45) Date of Patent: Sep. 3, 2002

(54) MATERIAL MELTING POINT DETERMINATION APPARATUS

(76) Inventor: Gregory R. Brotz, P.O. Box 1322, Sheboygan, WI (US) 53081

( * ) Notice: Subject to any disclaimer, the term of this patent is extended or adjusted under 35 U.S.C. 154(b) by 0 days.

(21) Appl. No.: 09/311,376

(22) Filed: May 13, 1999

(51) Int. Cl.$^7$ ............................................. G01N 25/04
(52) U.S. Cl. ...................... 374/17; 374/23; 250/341.1; 250/341.6
(58) Field of Search ............................ 374/17, 19, 23, 374/22, 24, 16; 250/341.6, 341.1; 702/135, 136, 134

(56) References Cited

U.S. PATENT DOCUMENTS

| | | | | |
|---|---|---|---|---|
| 1,184,837 A | * | 5/1916 | Edgecomb | 374/22 |
| 2,669,863 A | * | 2/1954 | Shapiro | 374/17 |
| 3,187,556 A | * | 6/1965 | Ehlers | 374/22 |
| 3,203,228 A | * | 8/1965 | Macklem | 374/22 |
| 3,412,599 A | * | 11/1968 | Hammons et al. | 374/17 |
| 4,481,418 A | * | 11/1984 | Vanzetti et al. | 250/338.1 |
| 4,804,274 A | * | 2/1989 | Green | 374/17 |
| 5,092,679 A | * | 3/1992 | Brotz | 374/17 |
| 5,288,148 A | * | 2/1994 | Rahimzadeh | 374/19 |
| 5,758,968 A | * | 6/1998 | Diebold | 374/17 |
| 6,231,228 B1 | * | 5/2001 | Brotz | 374/17 |

FOREIGN PATENT DOCUMENTS

| | | | | |
|---|---|---|---|---|
| JP | 208547 | * | 8/1990 | 374/16 |
| JP | 110455 | * | 5/1991 | 374/16 |
| JP | 186747 | * | 8/1991 | 374/16 |
| JP | 143645 | * | 5/1992 | 374/16 |

OTHER PUBLICATIONS

ASTM D 1525–58 T, "Tentative Method of Test for Vicat Softening Point of Plastics", pp. 559–561, 1958.*

* cited by examiner

Primary Examiner—Diego Gutierrez
Assistant Examiner—Stanley J. Pruchnic, Jr.
(74) Attorney, Agent, or Firm—William Nitkin (57) ABSTRACT

A device for determining the melting point of a sample material utilizing an infrared sensor to measure the temperature of the sample material and photocells to detect changes in transmissivity of the sample material at its melting point.

14 Claims, 6 Drawing Sheets

MATERIAL MELTING POINT DETERMINATION APPARATUS

BACKGROUND OF THE INVENTION

1. Field of the Invention

This invention resides in the area of apparatuses used for the determination of melting points of materials and more particularly relates to an apparatus which determines the melting point of a sample material by measuring the change in rate of wave transmission through the sample material and noting the temperature at which such change occurred.

2. Description of the Prior Art

Many devices are used to determine melting points of materials. The simplest are types where an observer notes the temperature at which a material, upon heating, becomes transparent. Such devices first involve immersing a particle of the material whose melting point is to be determined in a non-solvent which is heated at a known rate. As the heat from the medium is transferred into the particle, at the point where the temperature of the medium is equal to the melting point of the particle, the particle melts and changes its optical transmissibility. The recording of the temperature of the sample material while an observer monitors the reflectivity of light directed at such material is known in the art. A problem with many of these prior art melting point determination methods is that they lack accuracy in that they require the judgment of an observer as to when such a reaction has taken place, and this judgment can vary from observer to observer.

U.S. Pat. No. 5,092,679, by the present inventor, disclosed an apparatus and method that automatically records measurements of both light reflectivity and temperature of a material to determine its melting point. This invention also disclosed means for recording deformation of materials at various pressures.

Melting points are very important in determining a material's purity, especially in synthetic chemistry. The finer the melting point determination can be made, then the more accurately a purity determination can be made. This is especially helpful in the pharmaceutical industry where impurities may skew efficacy test results. Melting point apparatuses must be carefully designed to avoid any built-in accumulation of error.

SUMMARY OF THE INVENTION

It is an object of the device of this invention to determine the melting point of a sample material utilizing a light or infrared heat source and a photocell along with an electronic non-contact infrared thermometer.

It is a further object of this invention to provide a device that can also determine melting point as it relates to pressure on the sample material. It is important that pressure be considered when determining the melting point of some materials because under different pressures, a material may have a variety of states which affect its melting point.

In one embodiment, the device of this invention utilizes a powder made from the sample material that is to have its melting point determined. The powdered sample material is placed on a transparent glass slide on a stage above an infrared spot heater. Heat is then applied to the slide from below by the infrared spot heater, and the temperature of the sample material is measured by an infrared thermometer positioned above the sample material. The temperature of the sample material detected by the infrared thermometer can be continuously recorded. Around the infrared thermometer are disposed a plurality of photocells positioned to receive infrared waves which pass through the sample material. As the heat, which is increasing at a programmed ramped rate from the infrared spot heater, is directed on the sample material from below, the temperature of the sample material rises until the sample material melts, becomes fluid and spreads out, changing its transmissivity, i.e. percent of transmission of the infrared waves, such infrared waves passing through the slide and sample material thereon to be then detected by the photocells. When the photocells sense the change in rate increase or spike in the infrared rays, this change indicates that the temperature as then detected by the infrared thermometer at that point in time corresponds to the melting point of the sample material. A computer and chart recorder are attached to both the infrared thermometer and the photocells to record the activity of both to aid in determining the melting point of the sample material. It should be noted that multiple spectral bands and detectors other than infrared can be used in the apparatus of this invention.

DESCRIPTION OF THE PREFERRED EMBODIMENT(S)

Figure 1:
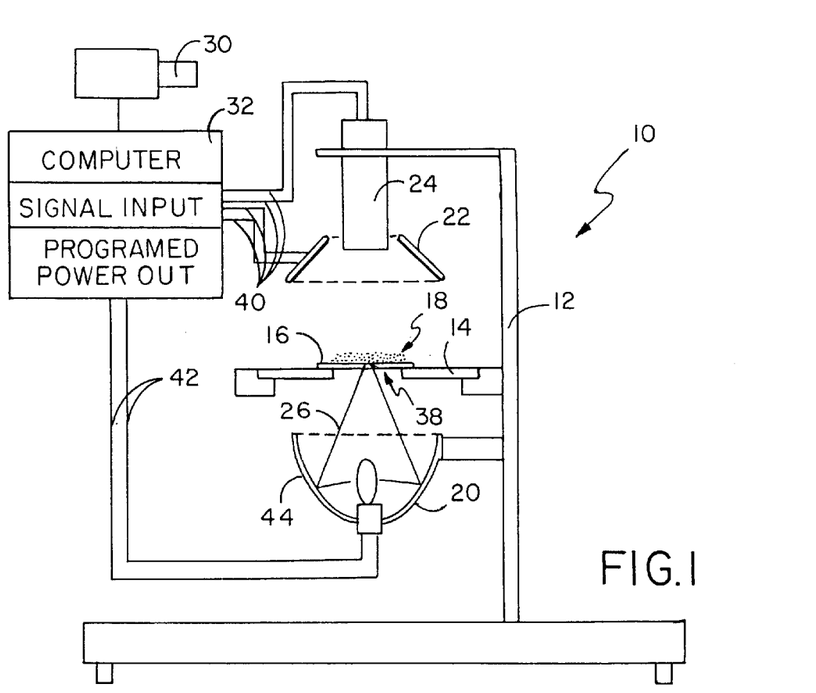
FIG. 1 illustrates a cross-sectional side view of one embodiment of the device of this invention.
Figure 2:
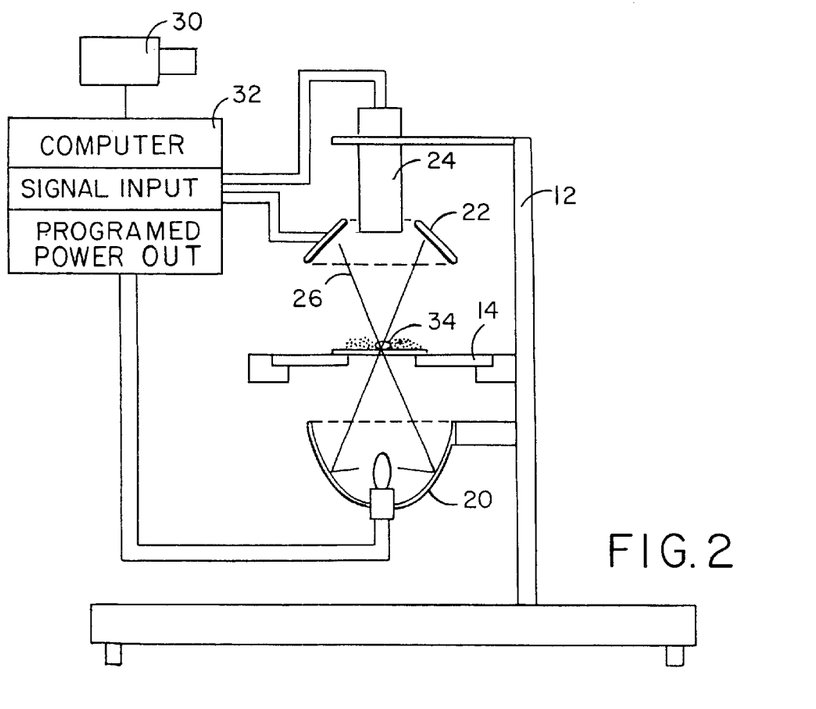
FIG. 2 illustrates the device of FIG. 1 showing the sample material melted.
Figure 10:
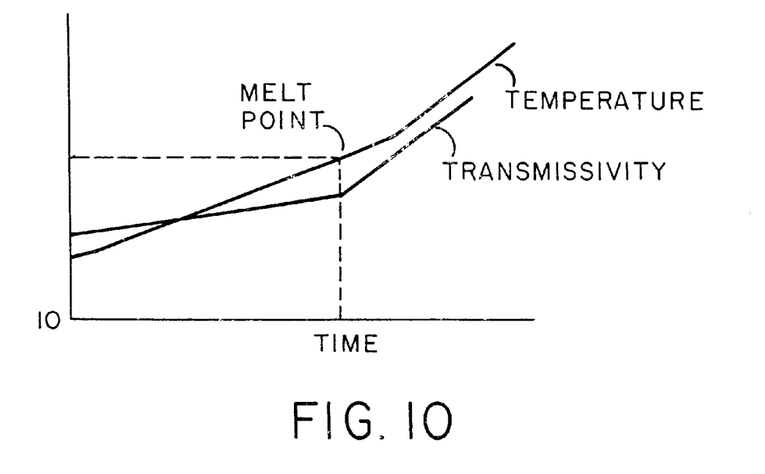
FIG. 10 illustrates a chart depicting changes in infrared transmissivity and the temperature of a sample material as it is being heated.

FIG. 1 illustrates one embodiment of the device and method of this invention. A sample of powdered material 18 whose melting point is to be determined is positioned on the upper surface of transparent slide 16. Although a powdered material is illustrated, the device of this invention will work on more solid forms of material, including films and slivers of material cut from blocks thereof. Melting points of sample material that are not solid at room temperature can be studied by providing for a cold stage to lower the sample material's temperature to where it is a solid. Such testing can also be done in an environmentally controlled chamber. Low-boiling organic liquids can be tested by the use of this device by first solidifying the sample material by cooling it to below its freezing point. For further reference, when the term "powdered material" is used, it should also be understood to include the more solid forms, as discussed above. Transparent slide 16 is made of an infrared-transparent, transmissive glass. Slide 16 is supported on horizontally disposed stage 14 which is attached at an adjustable height to vertically disposed support member 12. Beneath stage 14 centered under an opening 38 defined therein is infrared spot heater 20 which is also adjustably mounted in height on support member 12. Disposed above opening 38 and above sample material 18 is an infrared thermometer 24 which is surrounded by infrared-sensitive photocells 22 aimed at an angle toward opening 38, as will be described in further detail below. Infrared thermometer 24 can be of a non-contacting dual-color sensing type which is beneficial in resolving emissivity problems. Infrared thermometer 24 and photocells 22 are attached by signal input wires 40 to computer 32 which drives a chart recorder 30 making a chart printout and which also has power through lines 42 directing power to infrared spot heater 20. Infrared thermometer 24 senses the temperature of sample material 18 which is recorded on a chart printout produced by chart recorder 30. Photocells 22, as seen in FIG. 1, receive an initial low level of infrared waves 26 from infrared spot heater 20 since the sample material tends to block some of the transmission by absorption, scattering and reflection of such infrared waves 26. Heat produced by infrared spot heater 20 increases in intensity and can utilize a parabolic reflector 44 therein to help focus its rays on the sample material to be melted. As the heat increases on the sample material to be melted, the temperature of the sample material will finally reach the sample material's melting point. When this occurs, the sample material melts and flows which action changes its transmissivity to infrared waves, thus allowing more infrared waves 26 to pass through melted sample material 34, as seen in FIG. 2, and to be directed onto, and sensed by, photocells 22. This sensing of the increased levels of infrared waves 26 by photocells 22 will be reflected by a change in rate of increase of infrared waves in the chart printed by chart recorder 30 such that a comparison of when such a sensing of the rate increase first occurred with the observation of the temperature when the rate increase occurred, as detected by infrared thermometer at that point in time, will provide the observer with the melting point of the sample material being tested, as seen in FIG. 10. The spot heater emission spectrum should be wider than just infrared and can extend into optically visible light for the photocells to detect. A circular array of photo sensors with different spectral sensitivities can be used. It should also be noted that although the spot heater can use different sources, such as a glowing rod which would yield a narrow infrared spectra, the present invention can use a halogen bulb which produces an emission spectrum having wavelengths in multiple bands. The difference in infrared transmission of the sample material in its particulate state and its fluid state can be due to particles scattering the waves and the latter fluid's optical clarity. However, at the exact melting point of the sample material, one can see a flattening out of the temperature rise of the sample material due to the added energy absorption of the sample material needed to cause the breaking of crystal lattice bonds during phase transition. This flattening of the temperature rise was previously detectable only in dual cell thermal calorimetry until recent advances in thermophotometry due to the higher sensitivity level of present day photodetectors.

Infrared spot heater 20 and photocells 22 can further be of types that send and detect wavelengths other than infrared as this device not only monitors the sample material temperature through the non-contacting infrared thermometer 24, which is heat intensity sensitive, but also detects the transmissivity of the sample material by the photocells which are wavelength sensitive. Other non-contacting thermal detectors can be utilized including thermopiles, bolometers, and pyroelectric and pneumatic temperature detectors in the apparatus and method of this invention.

Figure 3:
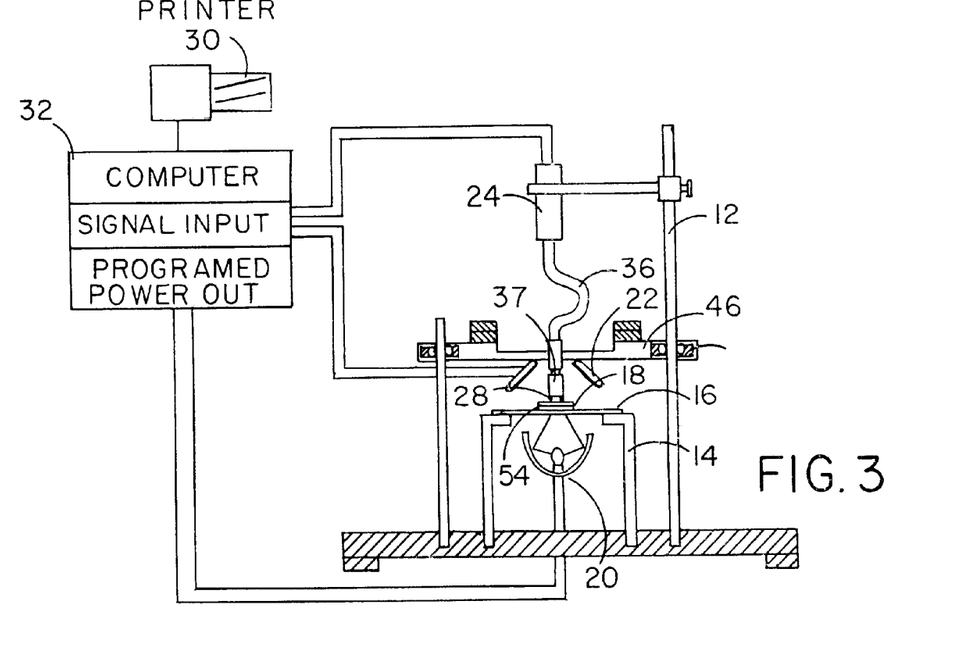
FIG. 3 illustrates a cross-sectional side view of an alternate embodiment of the device of this invention.
Figure 4:
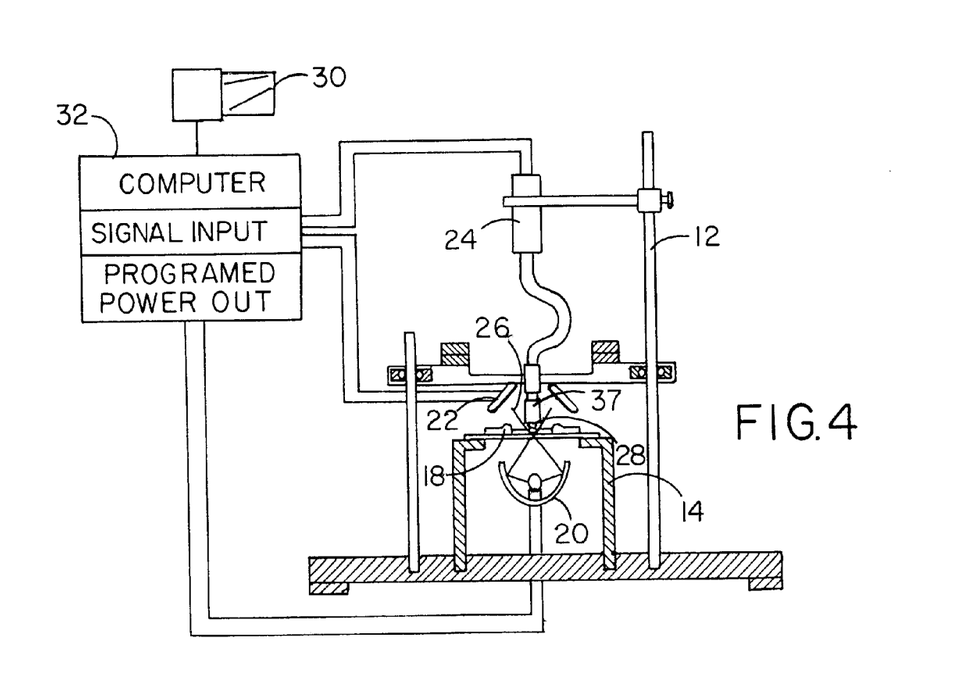
FIG. 4 illustrates the device of FIG. 3 showing the sample material melted.
Figure 6:
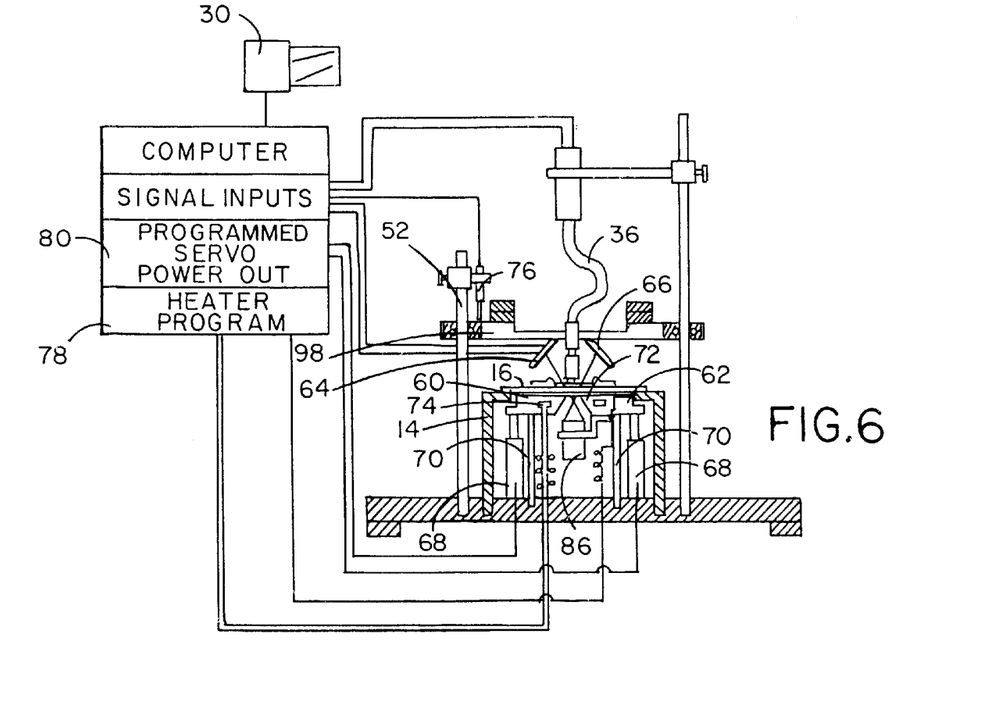
FIG. 6 illustrates a cross-sectional side view of a device using the heater of FIG. 5 and a stage movement detector.

The use of pressure applied to the sample material during testing can be helpful in some embodiments. In FIG. 3 infrared thermometer 24 extends to plate 46 by flexible fiber optic cable 36 terminating in end member 37. Plate 46 has weights 48 thereon. Plate 46 rides on bearings 50 on a pair of upright support members 12 and 52. Flexible fiber optic cable 36 interconnects infrared thermometer 24 to end member 37 resting on cover slide 54. Sample material 18, as seen in FIG. 3, has not yet melted. In FIG. 4 the sample material 18 has melted and weights 48 have moved plate 46 downward, pressing end member 37 on top of cover slide 54, forcing sample material 18 out from under cover slide 54, changing the transmissibility of sample material 18 within the sample plate sandwich and causing an increase in the passing of infrared waves 26 therethrough to cause an increase in the output of photocells 22. In one embodiment, three conical pins 28 extending between end member 37 of fiber optic cable 36 and cover slide 54 can be disposed therebetween to provide for an air gap between the top of cover slide 54 and the bottom of end member 37 of fiber optic cable 36 to prevent the fiber optic cable from acting as a heat sink which might otherwise draw heat away from the sample material. In some instances it is desirable to sense the movement of stage 14, and a motion detector 76 such as an LVDT (linear variable differential transformer) can be slidably attached to guide rod 52 as shown in FIG. 6.

Figure 5:
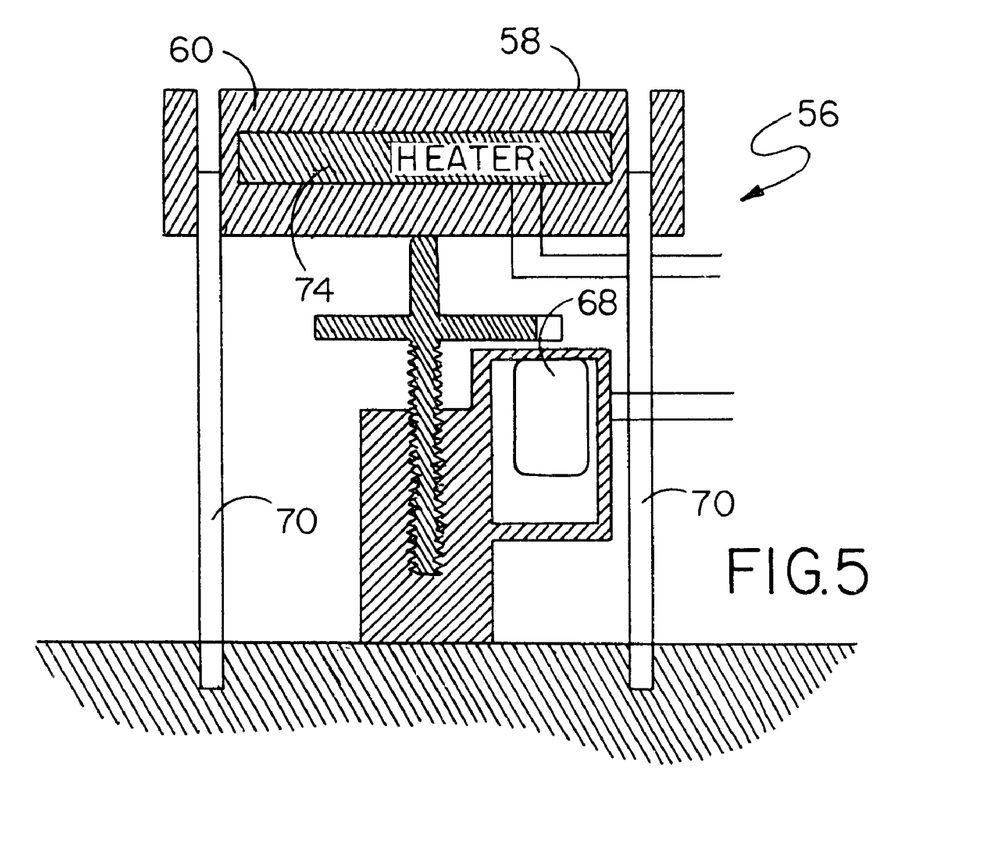
FIG. 5 illustrates a cross-sectional side view of an alternate heater embodiment.

One problem that can sometimes be encountered in the operation of the device of this invention is that the cover slide can allow a thermopile effect to occur because heat is lost faster at the edges of the cover slide than at its center such that the sample material melts in the center first because the outer area of the sample has not yet melted and there is no immediate flowing outward and thinning of the sample material at the melting point. One way of preventing this problem from occurring is to use a flat electrical resistance heater 56, as seen in FIG. 5, which is disposed under the stage in place of the infrared spot heater. Such heater's top plate 58 can be much larger in diameter than the diameter of the slide, not shown, so that heat energy would flow inward to the sample material to counter the thermopile effect. To avoid uneven heating, a massive heat block 60 can be utilized to help cause the sample material to melt all at once.

Massive heat block 60 can be positioned on a pair of heat block supports on which it can be driven up and down by a motor-driven linear drive 68 at a determined rate or ramped rate. Heat block 60 can be positioned at a desired distance from the overlying cover glass 54 under the flexible fiber optic cable 36, neither of which is shown in FIG. 5. The position of heat block 60 can be determined by the computer which actuates linear drive 68 up or down to create or close the gap between the heater and the bottom of transparent slide 16 which is supported on stage 14, as seen in FIG. 6. In FIG. 6 one can see heat block 60 positioned up against the bottom of transparent slide 16 while in FIG. 7 heat block 60 is shown moved downward away from transparent slide 16 by its linear drive 68. Heat block 60 can be heated by having heater 74 positioned therein. In the embodiments shown in FIGS. 6 and 7 heat block 60 has an aperture 72 formed therein above a frequency-tunable light source 86.

Another way to solve the irregular heating/melting problem is to provide a scanned heat beam directed onto the sample material. The scanner can take the form of a shaped reflector mounted on a rotating shaft at an angle such that more beam time is spent on areas of the sample material that would tend to melt last. This procedure will cause the sample material to melt more evenly and simultaneously as a whole. Other types of scanning systems such as dual axis galvo scanners can be used, and both laser beams and spot heater sources can be used with such scanners.

A shift or change in amplitude in any of the transmission spectra lines can provide useful information as to when a change from a solid to a molten state is occurring or if there is any chemical reactivity occurring or molecular bonds breaking or forming. Because the source emission spectrum should remain constant during the life of the spot heater bulb, its spectrograph can be held in the electronic memory in the central processing computer for the system. The spectrum detected from the photodetectors positioned after the sample spectra minus the source spectra yields the absorption spectrum of the sample material. An initial absorption spectrum saved at the beginning of a determination compared with saved absorption scans during the melting transition can provide phase change onset information along with crystallographic and even chemical information of a sample material.

Figure 7:
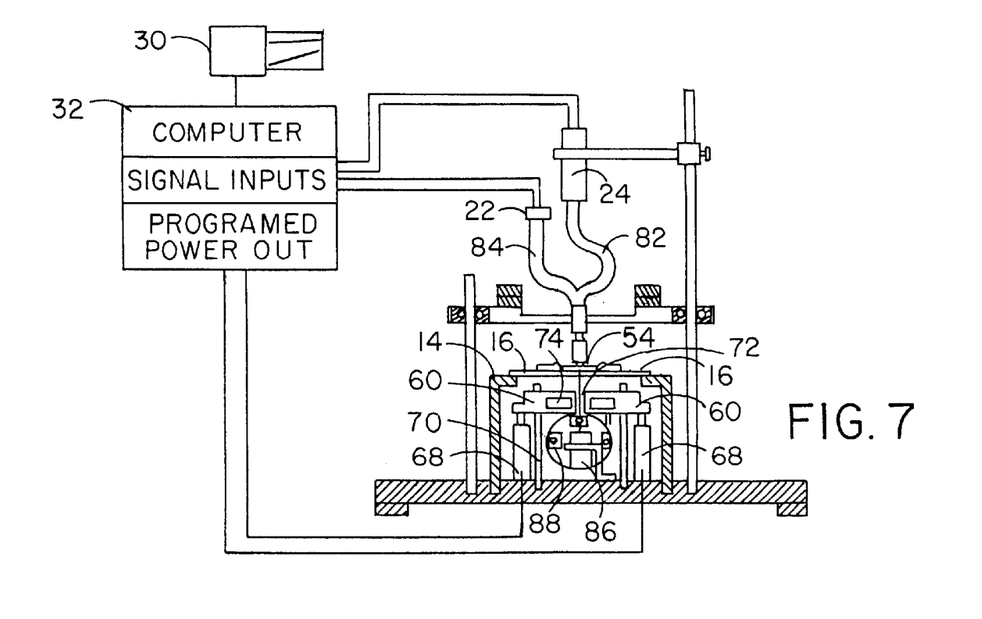
FIG. 7 illustrates a cross-sectional side view of a device using the heater of FIG. 5 and a split fiber optic cable to an infrared thermometer and a photocell.

FIG. 6 also illustrates an alternate embodiment of the invention where a fast divergent, tunable light source 86 produces a divergent beam which can be tunable to produce light at various wavelengths at different times which beam can be sensed by photocells having different wavelength sensitivities such as photocell 64 which can sense a different wavelength of light from those sensed by photocell 66. This feature is useful when determining the melting points of agglomerates or material made up of mixtures of materials having different melting temperatures. One way of producing different wavelengths at different times is to utilize a full spectral wavelength content light source with a carousel device 88, as seen in FIG. 7, positioned between the light source and the sample material, such carousel carrying a number of filters, each allowing the passage of a different wavelength. By rotating carousel device 88, one can position the desired filter between the light source and the sample material. The rotation of the carousel and filter positioning can be controlled by computer 32 so that the sensing by the photocell(s) and the infrared thermometer will be matched in time.

FIG. 7 shows a further alternate embodiment using a low divergence beam and where the fiber optic cable extends from cover slide 54 and bifurcates into a first fiber optic cable 82 extending to infrared thermometer 24 and a second fiber optic cable 84 extending to photocell 22.

Computer 32 can be utilized to adjust for time differences in melting the sample material from the bottom to the top of such material. Sample material thickness without such computerized adjustment can affect the accuracy of the temperature measurement. Thicker samples can start to melt from the underside before the upper surface of the material melts.

Materials generally melt at lower temperatures under pressure and in order to improve the accuracy and expand the practical scope of the device of this invention, pressure oscillation can be directed onto the sample material so that at the point just before the sample material would have melted without pressure, the sample material is forced in and out of a melted state by the application, and then release, of pressure on it. This alternating phase state is accompanied by corresponding changes in the sample material's opacity which is detected by the photocells.

Figure 8:
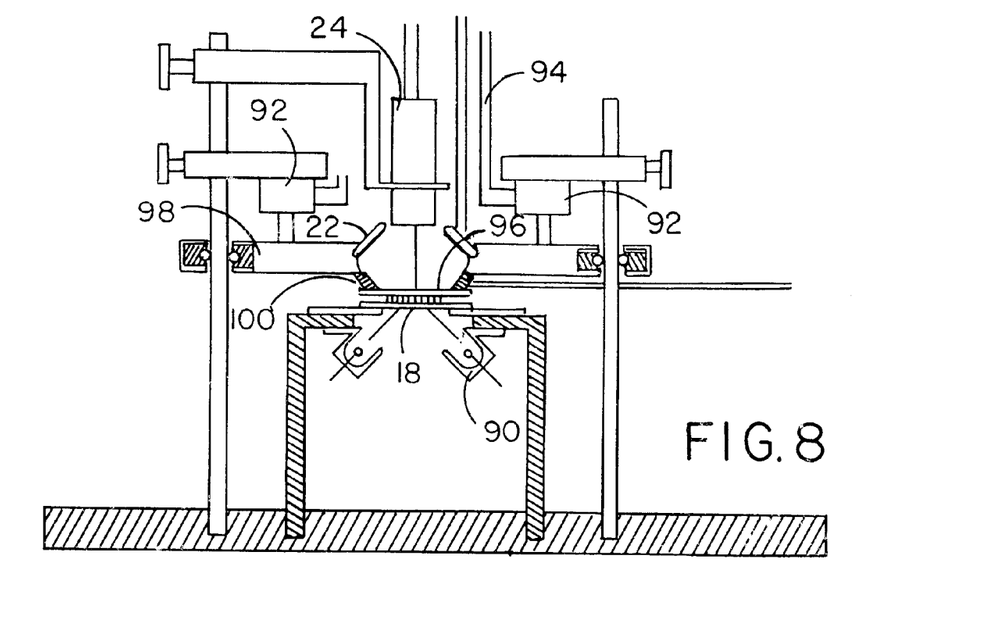
FIG. 8 illustrates a cross-sectional side view of a device utilizing a toroidal heat source and applying oscillating pressure on the sample material.
Figure 9:
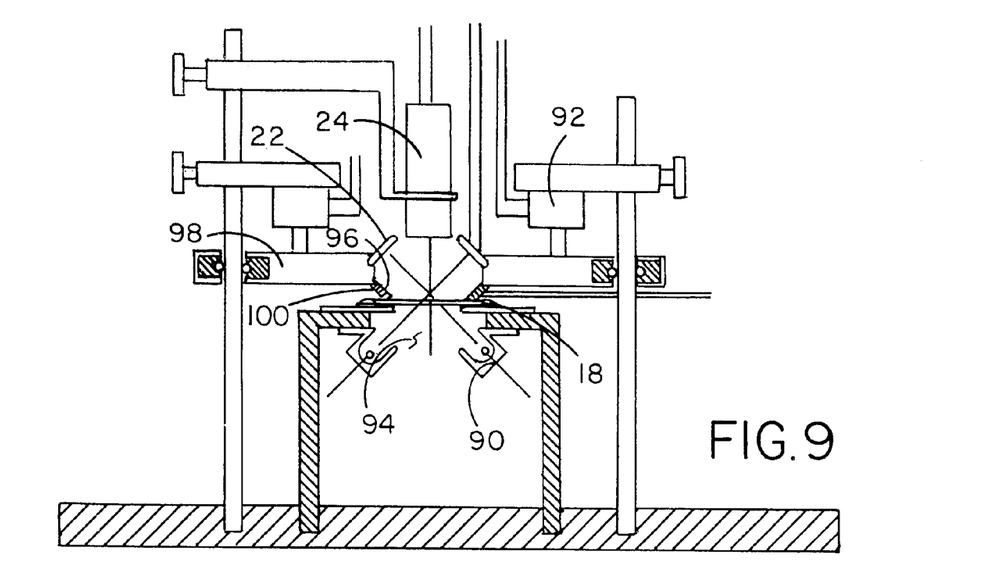
FIG. 9 illustrates the device of FIG. 8 showing the sample material melted.
Figure 11:
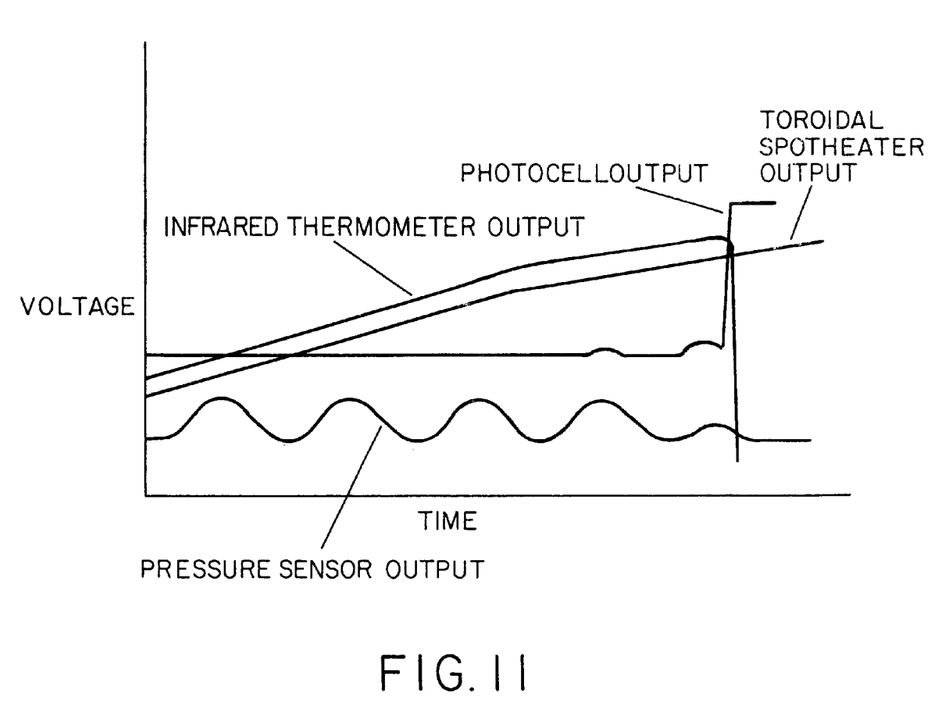
FIG. 11 illustrates a chart depicting changing temperature detected along with oscillating pressure.

In such an embodiment infrared thermometer 24 can be disposed above sample material 18 which sample material is under top cover 96. Linear actuators 92 apply pressure to pressure member 98 which applies pressure through arms 100 on top cover 96 disposed above sample material 18. In this embodiment various pressures are applied by the action of actuators 92 on pressure member 98. Such pressures can be oscillating, as seen in the chart of FIG. 11, depicted as pressure sensor output. FIG. 9 illustrates the embodiment of FIG. 8 wherein sample material 18 has melted and has been forced to the sides from under top cover 96, allowing toroidal heat source 90 to be sensed by photocells 22 and causing the photocell output to spike as seen in the chart of FIG. 11. During the pressure oscillations the photocell output has some small bumps corresponding to higher pressure periods of oscillation before the sample material melts, causing the photocell spike. At the same time infrared thermometer 24 no longer senses heated sample material 18 and further cannot sense toroidal heat source 90 as the infrared thermometer has a narrow field of view. Infrared thermometer 24 senses area 94 in which there is no heat-producing source directly in its path so that the infrared thermometer output, as depicted in the chart of FIG. 11, drops at the melting point of the sample material.

Although the present invention has been described with reference to particular embodiments, it will be apparent to those skilled in the art that variations and modifications can be substituted therefor without departing from the principles and spirit of the invention.

I claim:

1. An apparatus for determining the melting point of a material in an unmelted state, comprising:

a carrier having a first side and a second side on which said first side said material is deposited;

an infrared light wave heat source of sufficient intensity for melting said material, said heat source disposed below said second side of said carrier and directed at said material, said material when melted by said infrared light wave heat source changing its transmissivity to light at its melting point;

an infrared thermometer disposed on said first side of said carrier for detecting the temperature of said material;

at least one photocell disposed on said first side of said carrier in a position aligned with said infrared light wave heat source to detect changes in the percentage of transmission of light waves passing through said material;

means to determine said temperature detected by said infrared thermometer as said photocell detects a change in said material's percentage of transmission of light waves passing through said material as its transmissivity changes at its melting point, such temperature indicating said melting point of said material; and multi-channel means for recording said changes in transmissivity against said changes in temperature of said material.

2. The apparatus of claim 1 further including:

means to apply pressure on said material as said material is heated by said infrared light wave heat source, said pressure causing said material to spread as its melting point is being determined.

3. The apparatus of claim 1 wherein said infrared light wave heat source is a block heater.

4. The apparatus of claim 1 wherein said infrared light wave heat source is an infrared spot heater.

5. The apparatus of claim 2 wherein said means to apply pressure moves against said material, said apparatus further including means to measure and record the movement of said means to apply pressure on said material as said material melts and flows.

6. An apparatus for determining the melting point of a material in an unmelted state, comprising:
 a carrier having a first side and a second side on which said first side said material is deposited;
 an infrared light wave heat source of sufficient intensity for melting said material, said heat source disposed below said second side of said carrier and directed at said material, said material when melted by said infrared light wave heat source changing its transmissivity to light at its melting point;
 an infrared thermometer disposed on said first side of said carrier for detecting the temperature of said material;
 at least one photocell disposed on said first side of said carrier in a position aligned with said infrared light wave heat source to detect changes in the percentage of transmission of light waves passing through said material;
 means to determine said temperature detected by said infrared thermometer as said photocell detects a change in said material's percentage of transmission of light waves passing through said material as its transmissivity changes at its melting point, such temperature indicating said melting point of said material;
 multi-channel means for recording said changes in transmissivity against said changes in temperature of said material;
 means to apply pressure on said material as said material is heated by said infrared light wave heat source, said pressure causing said material to spread as its melting point is being determined wherein said means to apply pressure on said material further includes:
 a fiber optic cable directing said infrared waves to said infrared thermometer.

7. The apparatus of claim 6 wherein said fiber optic cable has at least one bifurcation directing said infrared waves to said photocell.

8. An apparatus for determining the melting point of a material in an unmelted state, comprising:
 a carrier having a first side and a second side on which said first side said material is deposited;
 an infrared light wave heat source of sufficient intensity for melting said material, said heat source disposed below said second side of said carrier and directed at said material, said material when melted by said infrared light wave heat source changing its transmissivity to light at its melting point;
 an infrared thermometer disposed on said first side of said carrier for detecting the temperature of said material;
 a first photocell disposed on said first side of said carrier in a position aligned with said infrared light wave heat source to detect changes in the percentage of transmission of light waves passing through said material;
 a second photocell able to detect different wavelengths from those detected by said first photocell;
 means to determine said temperature detected by said infrared thermometer as said first photocell detects a change in said material's percentage of transmission of light waves passing through said material as its transmissivity changes at its melting point, such temperature indicating said melting point of said material; and
 multi-channel means for recording said changes in transmissivity against said changes in temperature of said material.

9. The apparatus of claim 8 wherein said infrared light wave heat source can be tuned to produce light at various selected wavelengths.

10. An apparatus for determining the melting point of a material in an unmelted state, comprising:
 a carrier having a first side and a second side on which said first side said material is deposited;
 an infrared light wave heat source of sufficient intensity for melting said material, said heat source disposed below said second side of said carrier and directed at said material, said material when melted by said infrared light wave heat source changing its transmissivity to light at its melting point;
 an infrared thermometer disposed on said first side of said carrier for detecting the temperature of said material;
 at least one photocell disposed on said first side of said carrier in a position aligned with said infrared light wave heat source to detect changes in the percentage of transmission of light waves passing through said material;
 means to determine said temperature detected by said infrared thermometer as said photocell detects a change in said material's percentage of transmission of light waves passing through said material as its transmissivity changes at its melting point, such temperature indicating said melting point of said material;
 multi-channel means for recording said changes in transmissivity against said changes in temperature of said material;
 means to apply pressure on said material as said material is heated by said infrared light wave heat source, said pressure causing said material to spread as its melting point is being determined;
 wherein said means to apply pressure moves against said material, said apparatus further including means to measure and record the movement of said means to apply pressure on said material as said material melts and flows; and
 wherein said means to apply pressure against said material oscillates in the amount of pressure applied.

11. A process for determining the melting point of a material, comprising the steps of:
 placing said material between infrared-transparent carriers;
 directing an infrared light wave heat source at said material sufficient for melting said material, such material prior to melting blocking transmission of infrared light waves;
 detecting the temperature of said material with an infrared thermometer;
 melting said material;
 changing the infrared light transmissivity of said material upon said melting, allowing transmission of infrared light waves therethrough;
 detecting said infrared light waves passing through said material with at least one photocell; and
 determining said temperature of said material at the point of said infrared light wave detection, said temperature corresponding to the melting point of said material.

12. The process of claim 11 further including the step of:
 applying pressure to said carriers during said step of melting said material.

13. The process of claim 11 further including the steps of:
 measuring the transmission spectrum of said infrared-transparent carriers alone;

measuring the combined transmission spectrum of said infrared-transparent carriers and said material; and subtracting said transmission spectrum of said infrared-transparent carriers from the combined transmission spectrum of said infrared-transparent carriers and said material to determine the absorption spectrum of said material.

14. A process for determining the melting point of a material, comprising the steps of:

placing said material between infrared-transparent carriers;

directing an infrared light wave heat source at said material sufficient for melting said material, such material prior to melting blocking transmission of infrared light waves;

detecting the temperature of said material with an infrared thermometer;

melting said material;

changing the infrared light transmissivity of said material upon said melting, allowing transmission of infrared light waves therethrough;

detecting said infrared light waves passing through said material with a first photocell;

determining said temperature of said material at the point of said infrared light wave detection, said temperature corresponding to the melting point of said material;

utilizing infrared light of multiple different wavelengths;

providing a second photocell of different wavelength sensitivity from that of said first photocell; and detecting said different wavelengths of infrared light waves by said first and second photocells.

* * * * *